United States Patent [19]

Bilotti

[11] Patent Number: 4,589,582
[45] Date of Patent: May 20, 1986

[54] CARTRIDGE AND DRIVER ASSEMBLY FOR A SURGICAL STAPLING INSTRUMENT

[75] Inventor: Federico Bilotti, Madeira, Ohio

[73] Assignee: Senmed, Inc., Cincinnati, Ohio

[21] Appl. No.: 643,803

[22] Filed: Aug. 23, 1984

[51] Int. Cl.⁴ ............................................. A61B 17/00
[52] U.S. Cl. ............................. 227/19; 227/DIG. 1; 227/135
[58] Field of Search ............... 128/334 R, 334 C, 335; 227/DIG. 1, 19, 135

[56] References Cited

U.S. PATENT DOCUMENTS 4,244,372 1/1981 Kapitanov et al. ................. 227/19 X
4,527,724 7/1985 Chow et al. ........................ 227/19 X Primary Examiner—Paul A. Bell
Attorney, Agent, or Firm—Frost & Jacobs

[57] ABSTRACT

An improved cartridge and driver assembly is provided for a surgical stapling instrument of the type which drives staples through tissue to be joined and against an anvil to form the staples. The cartridge has a forming pocket or slot for each staple to be driven by a single actuation of the surgical stapling instrument. Each forming pocket is of elongated, transverse, biconvex cross-section, terminating in ends adapted to frictionally receive the legs of a surgical staple. The driver comprises a tine for each forming pocket, shiftable within the forming pocket to engage the crown of the staple to drive the staple from its forming pocket. Each driver tine is of substantially biconvex transverse cross-sectional configuration. Each forming pocket of the cartridge is of matching biconvex configuration to slidably receive its respective driver tine so that the tine engages the staple crown including those portions thereof directly over the staple legs.

12 Claims, 14 Drawing Figures

CARTRIDGE AND DRIVER ASSEMBLY FOR A SURGICAL STAPLING INSTRUMENT

TECHNICAL FIELD

The invention relates to an improved cartridge and driver assembly for a surgical stapling instrument of the type which drives staples through tissue to be joined and against an anvil to form the staples, and more particularly to such a cartridge and driver assembly wherein the driver tines have a transverse cross-sectional configuration which is substantially biconvex and the forming pockets of the cartridge have matching substantially biconvex configurations.

BACKGROUND ART

In recent years there has been an increasing number of surgeons using surgical staples, rather than conventional sutures. This is true because the use of surgical staples and surgical stapling instruments has made many difficult procedures much simpler. Of even more importance, however, is the fact that the use of surgical staples significantly reduces the time required for most procedures, and therefore reduces the length of time for which a patient must be maintained under anesthetic.

Many types of surgical stapling instruments have been developed for many different procedures. The present invention is directed to that type of surgical stapling instrument which has a cartridge and driver assembly and an anvil in opposed spaced relationship to the cartridge. Tissue to be joined is located between the cartridge and the anvil. The distance between the cartridge and the anvil is adjustable. When tissue to be joined is located between the cartridge and the anvil, and the distance therebetween is adjusted to be within the operational or working gap of the instrument, the driver can be actuated to drive the staple or staples from the cartridge, through the tissue to be joined, and against the anvil to form the staple or staples. The working gap of the instrument is that range of distances between the cartridge and the anvil within which proper forming of the staple is assured.

There are a number of such surgical stapling instruments. One non-limiting example of such a surgical stapling instrument is an intraluminal anastomosis surgical stapling instrument. U.S. Pat. No. 4,319,576 teaches an exemplary surgical stapling instrument of this type. Another non-limiting example of a surgical stapling instrument to which the teachings of the present invention are directed is a linear surgical stapling instrument. An example of such an instrument is taught in U.S. Pat. No. 4,527,724. A linear surgical stapling instrument is one in which a single actuation of the instrument implants and forms at least one rectilinear row of surgical staples. While not intended to be so limited, for purposes of an exemplary showing the present invention will be described in terms of its application to a linear surgical stapling instrument. Such an instrument is used on many different organs and tissues such as the lung, the esophagus, the stomach, the duodenum and throughout the intestinal track.

It is common for linear surgical stapling instruments of the type taught in the above identified copending application to be provided with cartridge and driver assemblies so configured that two linear rows of surgical staples are implanted when the instrument is actuated, one row being lngitudinally staggered with respect to the other. This requires a cartridge having two rows of forming pockets, each containing a surgical staple, and a driver having two rows of tines to provide a driver tine for each cartridge forming pocket. In their most usual configuration, each forming pocket is rectangular transverse cross section, with a groove at each end adapted to receive and frictionally retain the legs of a staple. Each driver tine is also rectangular in cross-section having considerable clearance in its respective forming pocket and being adapted to engage the crown portion of its respective staple between the legs thereof. This construction has certain drawbacks.

First of all, it is commonplace to make the cartridge and the driver of injection molded plastic material. Both structures are complex in configuration and require careful molding techniques. Since the driver tines have to be quite small to fit within the cartridge, it is difficult to make them of adequate strength. The transverse cross sectional configuration of the cartridge forming pockets is such that a staple could be loaded in the pocket in skewed fashion, as will be explained hereinafter. Furthermore, each driver tine engages its respective staple along the crown thereof between the staple legs, and not over the staple legs themselves which is most desirable. In some instances an improperly formed staple could have its crown re-enter its forming pocket, jamming into its driver or between the driver and the adjacent surface of its forming pocket.

The present invention is based upon the discovery that if the individual driver tines are configured to have a substantially biconvex cross-section and if the forming pockets in the cartridge are provided with corresponding biconvex shapes, the above noted deficiencies can be greatly reduced or eliminated. First of all, the strength of the individual driver tines is increased by increasing the width with respect to the length of the driver tine cross-section. Furthermore, when the driver tines and cartridge are made of plastic, the molding flow is improved. The possibility of improper staple loading is eliminated and the chances of jamming by an improperly formed staple is greatly reduced. There is better guidance of the staple and the driver tine in each cartridge forming pocket, and each driver tine engages its respective staple over the staple legs, where the driving force is most needed. Finally, both the driver and the cartridge have a better appearance. In addition, the substantially biconvex shape of the cartridge forming pockets allows the provision of more forming pockets in a given cartridge length and more staples in a given staple line, while maintaining strong cartridge construction, since there is more material between adjacent forming pockets than there would be with rectangular forming pockets.

DISCLOSURE OF THE INVENTION

According to the invention there is provided an improved cartridge and driver assembly for a surgical stapling instrument of the type which drives staples through tissue to be joined and against an anvil to form the staples. The cartridge has a forming pocket or slot for each staple to be driven by a single actuation of the surgical stapling instrument. The driver comprises a tine for each forming pocket, shiftable within its respective forming pocket to engage the staple therein and to drive the staple from its forming pocket.

In a first embodiment of the present invention, each driver tine has a substantially biconvex cross-sectional configuration with a small extension at each of its ends forming a longitudinal rail along the length of the tine at each end thereof.

Each forming pocket of the cartridge has a configuration corresponding closely to that of its driver tine, slidably receiving its driver tine with mininmum clearance. Thus, each forming pocket is of substantially biconvex configuration having a small groove at each end. These grooves are adapted to receive and frictionally engage and retain the legs of a surgical staple. These same grooves slidably receive the rail portions of their respective driver tines.

In a second embodiment, each driver tine is of a substantially biconvex cross-sectional configuration, terminating in narrow, rounded ends. Each forming pocket of the cartridge has a similar substantially biconvex configuration terminating in narrow rounded ends adapted to receive and frictionally retain the legs of a surgical staple. Again, the narrow rounded ends of the forming pocket slidably receive the narrow rounded ends of the driver tine.

In both embodiments, the driver tines are strengthened and when both the driver and the cartridge are molded of plastic, the molding flow is improved. Improper cross-loading of a staple in the cartridge forming pocket is no longer possible and the substantially biconvex configuration of each driver tine and its forming pocket provides better guidance for the driver tine and its respective surgical staple. In both embodiments each driver tine engages the crown of its respective staple together with that portion thereof which overlies the staple legs. In both embodiments the necessity for clearance between each driver tine and its respective forming pocket is reduced (since the driver tine is better guided in its forming pocket), greatly reducing the chances of jamming caused by an improperly formed surgical staple.

DETAILED DESCRIPTION OF THE INVENTION

Figure 1:
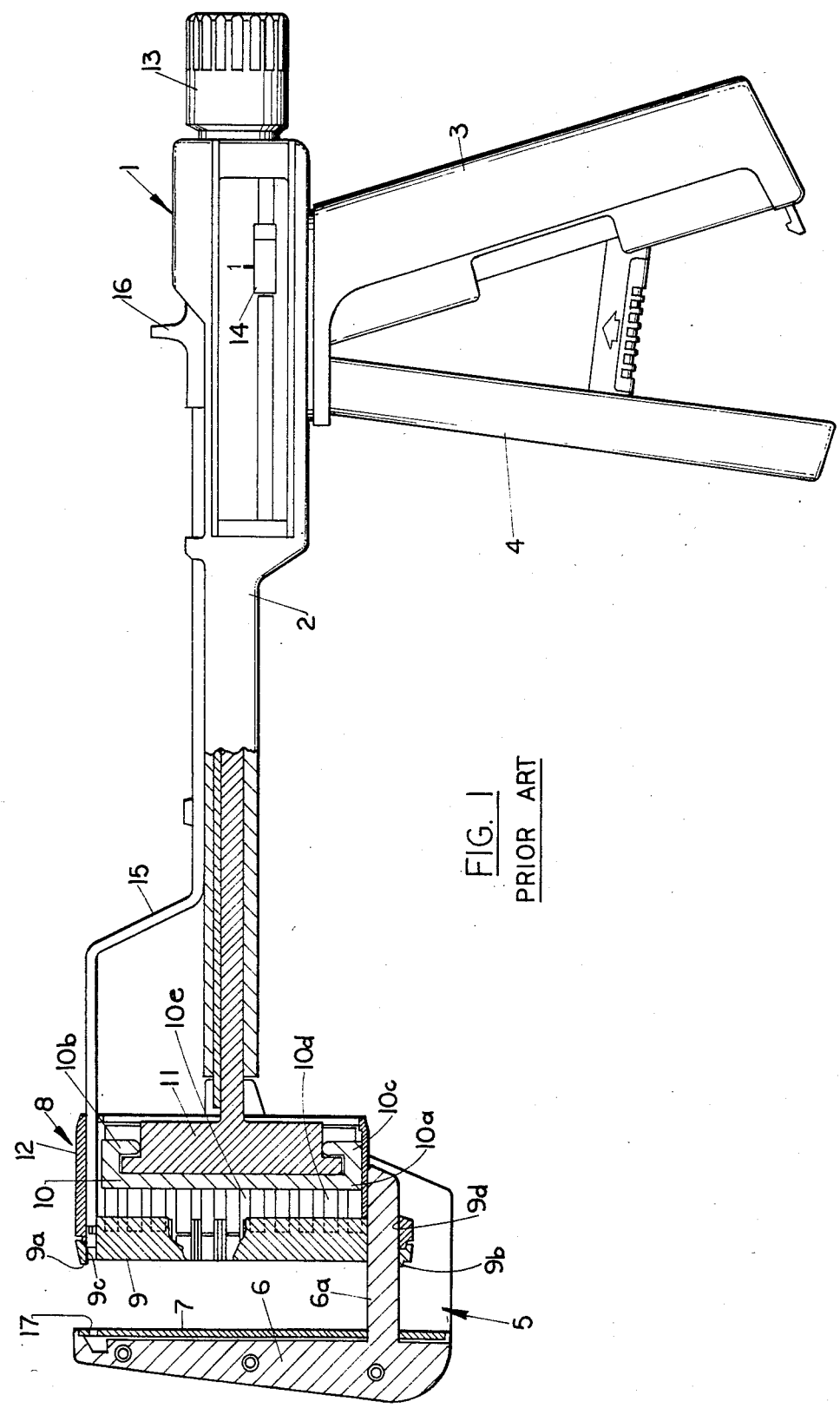
FIG. 1 is a side elevational view, partly in cross-section, illustrating an exemplary linear surgical stapling instrument.
Figure 2:
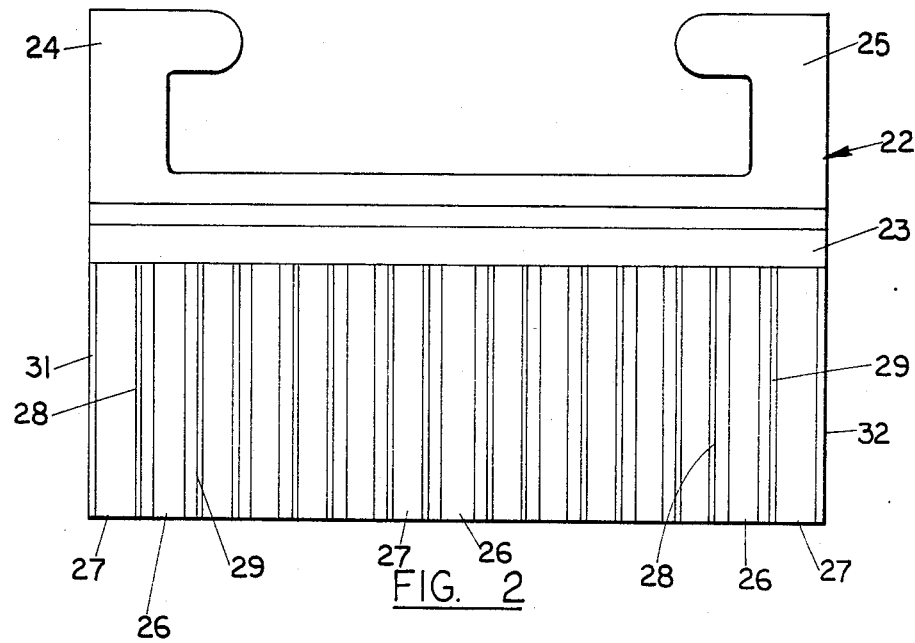
FIG. 2 is an elevational view of the driver of the present invention.
Figure 3:
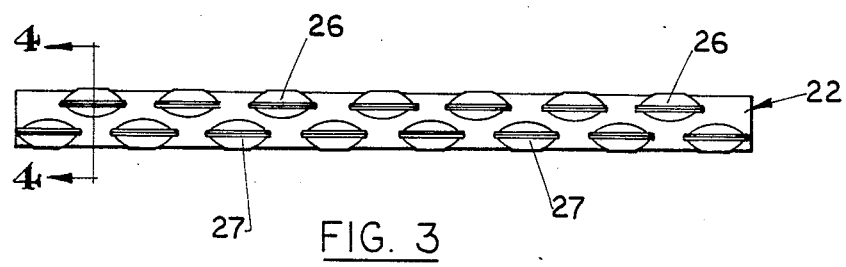
FIG. 3 is a bottom view of the driver of FIG. 2.
Figure 4:
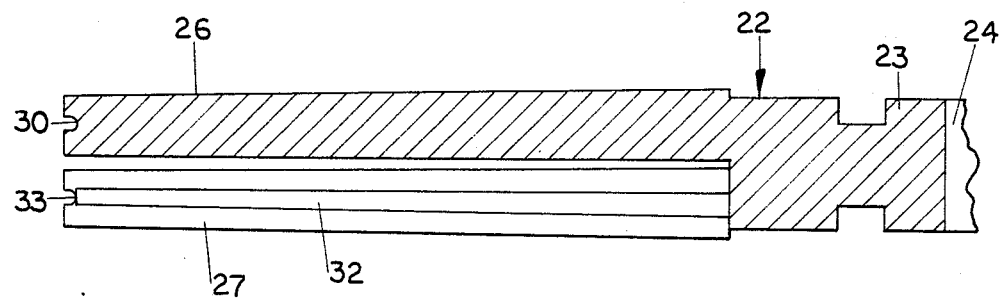
FIG. 4 is a cross-sectional view taken along section line 4—4 of FIG. 3.

As indicated above, for purposes of an exemplary showing, the teachings of the present invention will be set forth in their application to a linear surgical stapling instrument of the type described in U.S. Pat. No. 4,527,724. The teachings of this copending application are incorporated herein by reference. By way of background, reference is first made to FIG. 1 wherein a linear surgical stapling instrument of the type taught in the above noted copending application is illustrated. The instrument, generally indicated at 1, comprises a body 2 having a handle 3 and a trigger assembly 4. At its forward end, the instrument 1 is provided with a fixed jaw 5 including a pilot member 6 having an extension 6a and an anvil 7, having staple leg forming depressions (not shown) therein, as is conventional.

The instrument also has a movable jaw generally indicated at 8 comprising a cartridge 9, a driver 10, a driver rod 11 and a surrounding casing 12.

At its rearward end, the instrument has an adjustment knob 13 which is operatively connected to handle 3, trigger assembly 4 and movable jaw 8. When rotated in the proper direction, adjustment knob 13 causes the handle 3 and trigger assembly 4 to shift forwardly with respect to body 2 and additionally causes the movable jaw 8 to approach fixed jaw 5. As a result, the staple cartridge 9 approaches the anvil 7. The adjustment knob also is operatively connected to indicator means, one of which is shown at 14, which graphically shows the surgeon when the distance between cartridge 9 and anvil 7 is within the working gap of the instrument, assuring that the staples will be properly formed when the instrument is actuated. The cartridge 9 may be provided with stops 9a and 9b, cooperating with anvil 7 to determine the forwardmost position of movable jaw 8.

An alignment pin 15 is shiftably mounted on the instrument body 2, and extends through a perforation 9c in the cartridge 9 and casing 12. The alignment pin is manually shiftable to an operative position by the member 16. When in its operative position, the free end of alignment pin 15 extends through an opening 17 in anvil 7 and into fixed jaw 5. In this way, the alignment pin not only assures that the anvil 7 and cartridge 9 are properly oriented with respect to each other, but also traps the tissue (not shown) to be sutured between the anvil and the cartridge. The cartridge 9 has a rectangular opening 9d through which pilot extension 6a extends as an additional guide for the cartridge 9.

Figure 12:
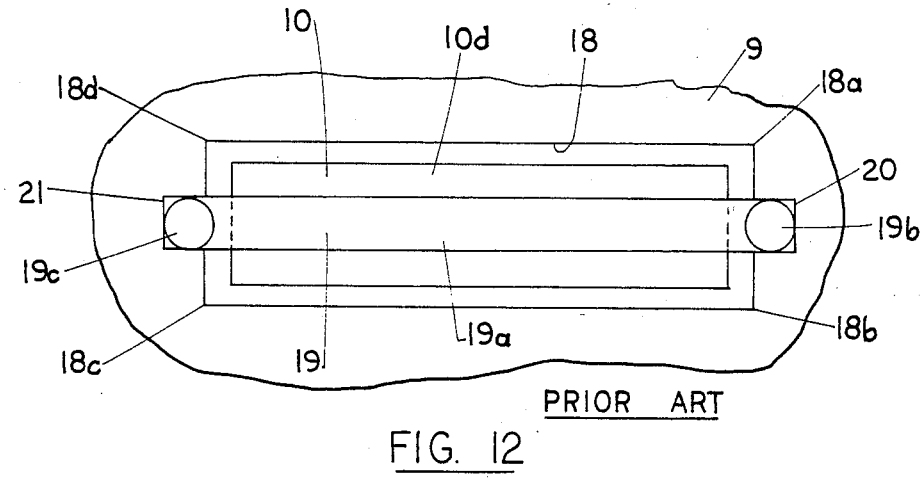
FIG. 12 is a fragmentary, bottom view of a prior art cartridge illustrating a forming pocket thereof containing a surgical staple and a driver tine.

The cartridge 9 has a plurality of forming pockets 18 therein, each having a surgical staple mounted therein (as shown in FIG. 12). In the embodiment described in the above noted U.S. Pat. No. 4,527,724, the cartridge has two staggered rows of forming pockets so that two staggered rectilinear rows of surgical staples are formed and implanted when the instrument is actuated. The driver 10 has a body 10a with two hook-shaped elements 10b and 10c by which it is connected to driver rod 11. The driver also has two rows of driver tines, one of which is shown at 10d. Thus, there is a driver tine located in each forming pocket of cartridge 9.

Driver 10, through the driver rod 11, is operatively connected to trigger assembly 4. When the tissue to be joined is located between anvil 7 and cartridge 9, when alignment pin 15 is in its actuated position, and when the distance between movable jaw 8 and fixed jaw 5 has been properly adjusted so that the distance between anvil 7 and cartridge 9 falls within the working gap of the instrument, the instrument can be actuated by squeezing trigger 4. The squeezing of trigger 4 will cause the driver rod 11 and the driver 10 to move forwardly, driving the staples within cartridge 9 out of the cartridge, through the tissue to be joined, and against anvil 7 which causes the free ends of the staple legs to be properly formed by the anvil forming depressions.

Reference is now made to FIG. 12. FIG. 12 is a fragmentary bottom or front view of the prior art cartridge 9, illustrating one of the forming pockets 18 therein. FIG. 12 also illustrates a surgical staple 19 and one of the tines 10d of driver 10.

It will be noted that the forming pocket 18 is of rectangular configuration, having additional grooves 20 and 21 at its ends. The surgical staple 19 is of typical U-shaped configuration, having a crown portion 19a and downwardly depending, parallel legs 19b and 19c. The legs 19b and 19c are frictionally engaged and retained in grooves 20 and 21, respectively.

The driver tine 10d is of rectangular configuration having considerable clearance with respect to forming pocket 18. The bottom of driver tine 10d overlies the crown 19a of surgical staple 19. It will be apparent that when the driver tine 10d is shifted forwardly (see FIG. 1) its engagement of staple crown 19a will cause the staple 19 to be driven out of forming pocket 18, through the tissue located between anvil 7 and cartridge 9, with the free ends of staple legs 19b and 19c entering and being formed by the anvil forming depressions.

It will be evident from FIG. 12, considering the very small size of surgical staple 19, that driver tine 10d is also quite small and narrow. It will further be noted from FIG. 12 that the driver tine 10d overlies and engages the central portion of staple crown 19a, but does not engage those portions of crown 19a which overlie staple legs 19b and 19c. Therefore, driver tine 10d does not exert force directly on the staple legs 19d and 19c.

Another problem encountered with the structure FIG. 12 is due in part to the clearance between driver tine 10d and the forming pocket 18. It is possible for the crown 19a to go past the driver tine 10d ends, wedging or jamming between driver tine 10d and forming pocket 18.

Yet another problem encountered with the structure of FIG. 12 is that of cross-loading of staple 19 in forming pocket 18 of cartridge 9. By this is meant that the staple legs 19b and 19c, instead of being frictionally engaged in grooves 20 and 21, are sometimes inadvertently frictionally engaged in diagonal corners 18a–18c or 18b–18d of forming pocket 18. When this occurs, the staple legs 19b and 19c will be misaligned with anvil forming depressions and the staple will be malformed.

Reference is now made to FIGS. 2–5 wherein the improved driver of the present invention is illustrated, and wherein like parts have been given like index numerals. The driver of the present invention is generally indicated at 22. The driver 22 has a body 23 substantially identical to the body 10a of driver 10 of FIG. 1. The body 23 has a pair of hook-shaped portions 24 and 25 equivalent to the hook-shaped portions 10b and 10c of FIG. 1. The hook-shaped portions 24 and 25 enable driver 22 to engage the driver rod 11.

For purposes of an exemplary showing, the driver 22 is illustrated as being of the type intended to drive two staggered rectilinear rows of surgical staples simultaneously. Thus, driver 22 has two staggered rows of driver tines 26 and 27. It will be understood by one skilled in the art that there could be more than two rows of driver tines, or there could be a single row thereof.

It will be noted that the tines 26 are essentially mirror images of the tines 27 and both are of substantially biconvex cross-section. The outboard sides of tines 26 have flats 26a formed thereon, and in similar fashion the outboard sides of tines 27 have flats 27a formed thereon.

Figure 5:
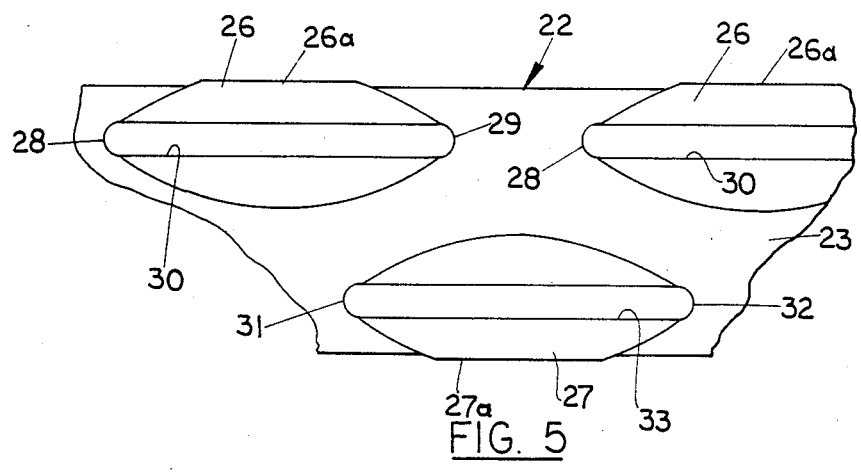
FIG. 5 is a fragmentary, enlarged bottom view of the driver of the present invention.
Figure 6:
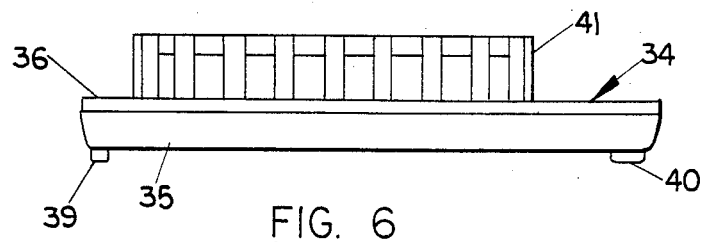
FIG. 6 is a side elevational view of the cartridge of the present invention.
Figure 7:
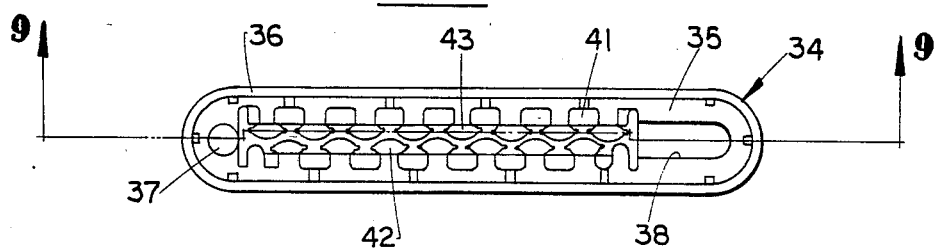
FIG. 7 is a plan view of the cartridge of FIG. 6.

As is most clearly seen in FIG. 5, the substantially biconvex cross-section of each tine 26 narrows near its ends and terminates in rounded extensions 28 and 29. As will be apparent from FIG. 2, the rounded extensions 28 and 29 form rails on the end edges of tines 26, extending the length thereof. On their bottom ends, the tines 26 may be provided with grooves 30 (see FIGS. 4 and 5) so sized as to just nicely engage the crown portions of their respective surgical staples.

As is evident from FIG. 5, the substantially biconvex configuration of tines 27 also terminate in rounded extensions 31 and 32, forming rails extending the length of the tines. The tines 27 are also provided with grooves 33 equivalent to the grooves 30 of tines 26.

The driver 22 having been described in detail, reference is now made to FIGS. 5–11 wherein the cartridge of the present invention is illustrated. Again, like parts have been given like index numerals. The cartridge of these figures is generally indicated at 34, and in many respects is quite similar to the cartridge 9 of FIG. 1.

The cartridge 34, like the driver 22, constitutes an integral, one-piece injection molded plastic member. While both the driver 22 and the cartridge 34 could be made of metal or the like, they lend themselves well to being formed of a plastic material of adequate strength, suitable for use in a surgical environment, and capable of sterilization by one or more of the known and well accepted methods. Such plastic materials are well-known in the art.

The cartridge 34 comprises an elongated body 35 having an upstanding surrounding flange 36. At one end, the body 35 has a circular perforation 37, similar to the perforation 9a of cartridge 9 of FIG. 1, and adapted to receive the alignment pin 15. At the other end, the body 35 is provided with an elongated slot or opening 38, equivalent to the slot 9d of cartridge 9 and adapted to receive the extension 6a of pilot 6. The body 35 is also provided with stop members 39 and 40, equivalent to stop members 9a and 9b of cartridge 9, and intended to serve the same purpose.

Figure 8:
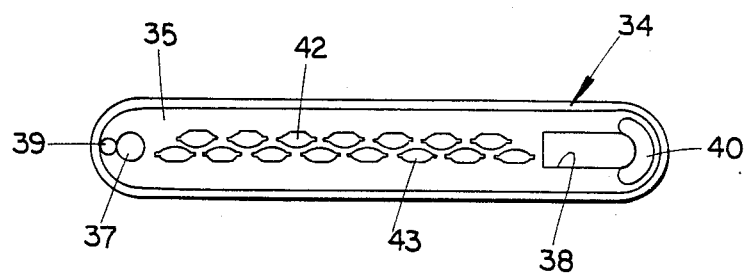
FIG. 8 is a bottom view of the cartridge of FIG. 6.
Figure 9:
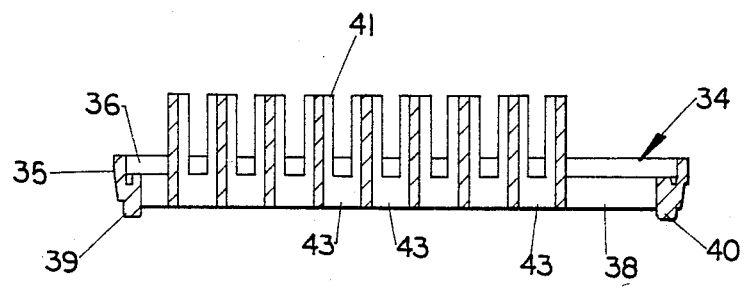
FIG. 9 is a cross-sectional view taken along section line 9—9 of FIG. 7.

The cartridge 34 has a centrally located, upstanding, longitudinally extending wall 41. Two rectilinear rows of forming pockets 42 and 43 are formed in the wall 41 and extend through the bottom surface of the cartridge 34, as shown in FIGS. 8 and 9. The forming pockets 42 are staggered with respect to the forming pockets 43 and the forming pockets 42 and 43 are mirror images of each other.

Figure 10:
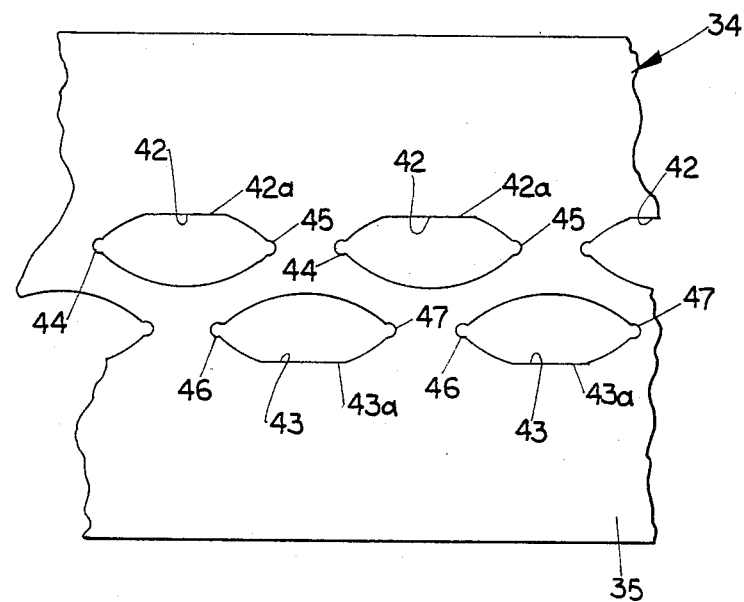
FIG. 10 is a fragmentary enlarged bottom view of the cartridge of FIG. 6.
Figure 11:
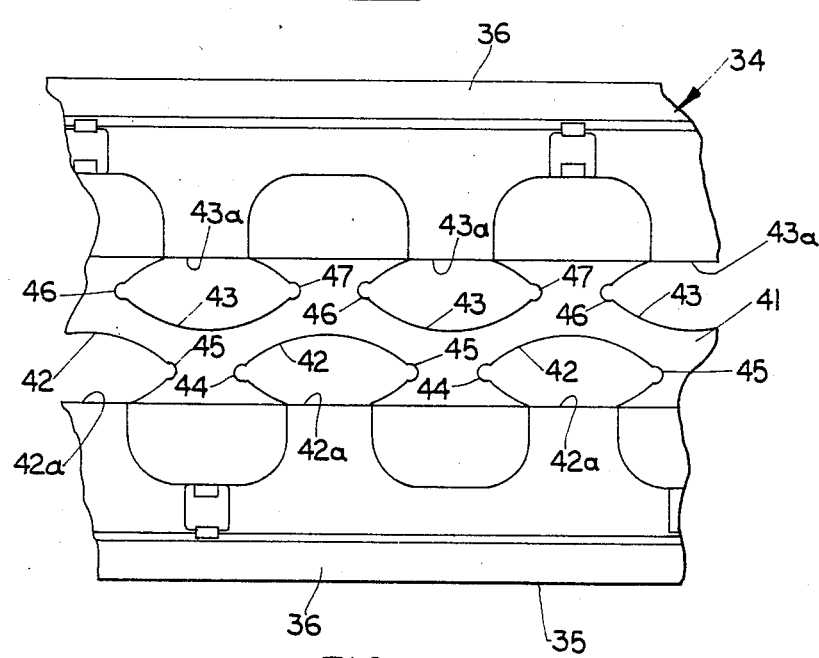
FIG. 11 is a fragmentary, enlarged plan view of the cartridge of FIG. 6.

As can readily be ascertained from FIGS. 10 and 11, when compared to FIG. 5, the peripheral configuration of forming pockets 42 corresponds to the peripheral configuration of driver tines 26, while the peripheral configuration of forming pockets 43 corresponds to the peripheral configuration of driver tines 27. To this end, forming pockets 42 having a substantially biconvex configuration with a flat 42a on one side, conforming to the flat 26a of driver tines 26. Each forming pocket 42 has rounded grooves 44 and 45 at its ends corresponding to the rounded extensions 28 and 29 of driver tines 26. In similar fashion, the forming pockets 43 of cartridge 34 are of substantially biconvex configuration having flats 43a corresponding to the flats 27a of driver tines 27 and having rounded grooves 46 and 47 at their ends corresponding to the rounded extensions 31 and 32 of driver tines 27. The forming pockets 42 and 43 of cartridge 35 are so sized as to just nicely receive the driver tines 26 and 27, respectively, with a minimum of clearance.

Figure 13:
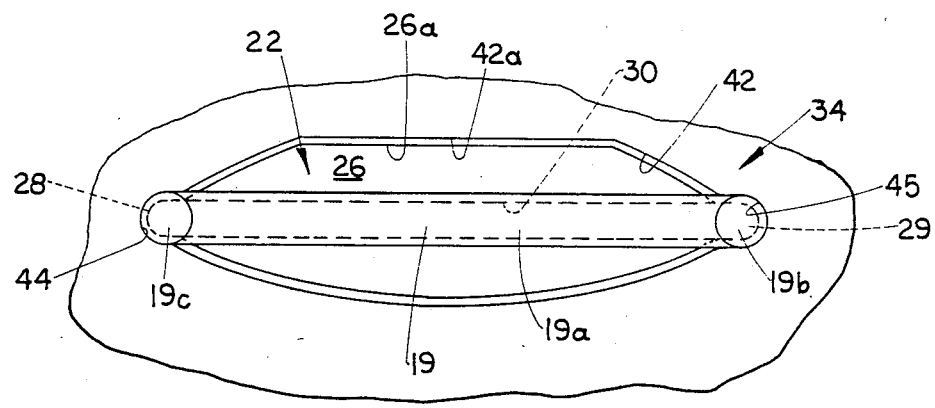
FIG. 13 is a fragmentary bottom view of the cartridge of FIGS. 6–11, similar to FIG. 12, and illustrating a forming pocket thereof together with a surgical staple and a driver tine therein.

Reference is now made to FIG. 13 which is a fragmentary bottom view of cartridge 34 showing one of the pockets 42, a driver tine 26 and an exemplary surgical staple similar to that of FIG. 12 and given like index numerals. It will be understood that a similar view of a cartridge forming pocket 43 and a driver tine 27 would be identical to FIG. 13, but a mirror image thereof.

It will be apparent from FIG. 13 that the rounded rail-like extensions 28 and 29 of driver tine 26 ride in the grooves 44 and 45 of forming pocket 42. Similarly, the legs 19b and 19c are frictionally engaged in these grooves. It will be immediately apparent from FIG. 13 that inadvertent cross-loading, of the type described above, cannot occur in the forming pocket 42. Since the extensions 28 and 29 of driver tine 26 are located in the grooves 44 and 45 of forming pocket 42, the clearances between the driver tine 26 and the forming pocket 42 could be greater than in the prior art cartridge 9 of FIG. 12, since the extensions 28 and 29 of driver tine 26 greatly reduce the chances of jamming by an improperly formed surgical staple.

By virtue of its increased dimensions, driver tine 26 will be stronger than driver tine 10d of FIG. 12. It will be noted that driver tine 26 overlies the crown portion 19a of staple 19, the crown portion 19a being partially received in the groove 30 of the driver tine 26. It will further be noted, however, that the driver tine extensions 28 and 29 overlie those portions of the crown 19a which are directly above legs 19b and 19c. As a consequence, a part of the force of the driver tine 26 is applied directly over legs 19b and 19c, as is most desirable. Finally, as will be apparent from FIG. 13, the shapes of the forming pocket 42 of cartridge 34 and the tine 26 of driver 22 are such that, when molded of plastic material, molding flow will be improved over that of the structure of FIG. 12, increasing the crispness of molding detail.

Figure 14:
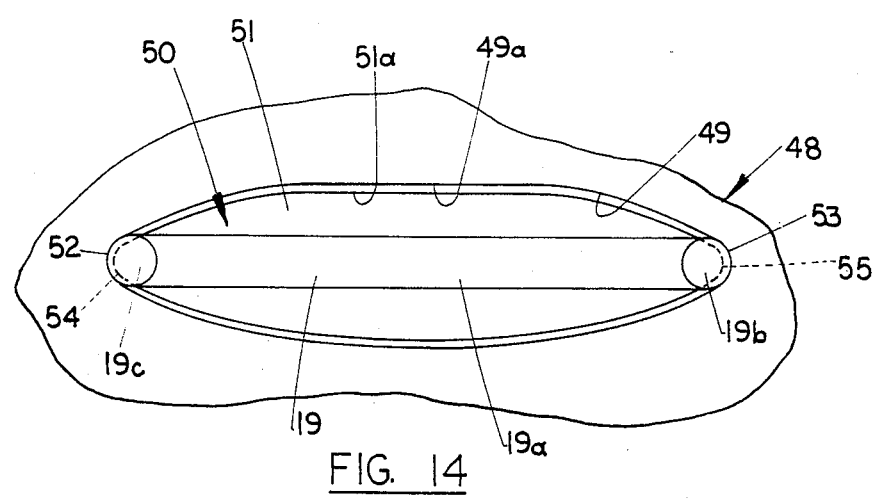
FIG. 14 is a fragmentary bottom view, similar to FIG. 13, but illustrating a second embodiment of a forming pocket containing a surgical staple and a second embodiment of a driver tine.

FIG. 14 is similar to FIG. 13 and illustrates a second embodiment of the present invention. FIG. 14 is a fragmentary bottom view of a cartridge generally indicated at 48 and having a forming pocket 49 corresponding to the forming pocket 42 of FIG. 13. FIG. 14 also shows a driver generally indicated at 50 and one of its tines 51. A surgical staple, identical to those of FIGS. 12 and 13 is shown, and like parts have been given like index numerals.

The cartridge 48 differs from the cartridge 34 only in the peripheral configuration of the forming pocket 49, which corresponds to forming pocket 42. In the cartridge 48 it will be understood that the forming pockets of the second row, corresponding to forming pockets 43 of cartridge 34, would be identical to the forming pocket 49, except a mirror image thereof. It is to be assumed that the driver 50 is identical to driver 22 in all respects except that of the peripheral configuration of its tines. Tine 51 is equivalent to tine 26b of driver 22. It will be understood that a tine of driver 50, equivalent to tine 27 of driver 22 would be identical to the tine 51, except a mirror image thereof.

The forming pocket 49 of cartridge 48 has a flat 49a equivalent to the flat 42a of FIG. 13. The forming pocket 49 differs from forming pocket 42 of FIG. 13 primarily in that its substantially biconvex configuration blends directly into rounded ends 52 and 53. The rounded ends 52 and 53 are equivalent to the rounded endmost portions of the grooves 44 and 45 of FIG. 13, but there are no distinct grooves, as such, in FIG. 14. The driver tine 51 of driver 50 differs from driver tine 26 of driver 22 (FIG. 13) in a similar fashion. To this end, driver tine 51 has a flat 51a equivalent to driver tine flat 26a. The substantially biconvex configuration of driver tine 51 blends directly into rounded ends 54 and 55, equivalent to the rounded endmost portions of extensions 28 and 29 of driver tine 26 (FIG. 13). Despite these differences, it will be immediately apparent that the structure of FIG. 14 will have all of the advantages described with respect to the structure of FIG. 13. The structure of FIG. 14 has the additional advantage in that the shape of driver tine 51 and forming pocket 49 is somewhat simpler than the shape of driver tine 26 and forming pocket 42.

Modifications may be made in the invention without departing from the spirit of it.

What is claimed is:

1. An improved staple-containing cartridge and driver assembly for a surgical stapling instrument for use with conventional U-shaped surgical staples having a crown portion and downwardly depending legs, said instrument being of the type having driver actuating means and an anvil opposed to said cartridge and which, when the driver actuating means is operated, a plurality of staples are driven from said cartridge through tissue to be joined and against said anvil to form said staples, said cartridge having a forming pocket for each staple, each of said forming pockets is of elongated transverse cross-section of substantially biconvex configuration terminating in ends adapted to frictionally receive and retain the legs of a surgical staple, a driver comprising an elongated tine for each forming pocket, each tine being shiftable in its respective forming pocket to drive said staple therefrom, each driver tine having an elongated substantially biconvex transverse cross-sectional configuration closely matching that of its respective forming pocket, each driver tine being configured to engage the crown portion of its respective staple including those portions of said crown above said staple legs.

2. The cartridge and driver assembly of claim 1 wherein said cartridge forming pockets and said driver tines are arranged in at least one row thereof.

3. The cartridge and driver assembly of claim 2 wherein said at least one row of cartridge forming pockets and driver tines is rectilinear.

4. The cartridge and driver assembly of claim 1 wherein said cartridge forming pockets and said driver tines are arranged in two parallel rows.

5. The cartridge and driver assembly of claim 4 wherein said rows are rectilinear and wherein said cartridge forming pockets and driver tines of one of said rows are staggered with respect to the cartridge forming pockets and driver tines of the other of said rows.

6. The cartridge and driver assembly of claim 1 wherein said elongated, transverse, substantially biconvex cross-section of each forming pocket terminates at its ends in grooves with rounded ends comprising said ends to frictionally receive and retain the legs of a surgical staple, said elongated transverse, substantially biconvex, cross-sectional configuration of each driver tine terminating in rounded end extensions slidably receivable in said forming pocket grooves and comprising rail-like members extending the length of said driver tine.

7. The cartridge and driver assembly of claim 6 wherein said cartridge forming pockets and said drive tines are arranged in two parallel rows.

8. The cartridge and driver assembly of claim 7 wherein said rows are rectilinear and wherein said cartridge forming pockets and driver tines of one of said rows are staggered with respect to the cartridge forming pockets and driver tines of the other of said rows.

9. The cartridge and driver assembly of claim 1 wherein said elongated, transverse, substantially biconvex cross-section of each forming pocket terminates in narrow rounded ends comprising said ends adapted to frictionally receive and retain the legs of a surgical staple, said elongated, transverse, substantially biconvex, cross-sectional configuration of each driver tine terminating in corresponding narrow rounded ends.

10. The cartridge and driver assembly of claim 9 wherein said cartridge forming pockets and said drive tines are arranged in two parallel rows.

11. The cartridge and driver assembly of claim 10 wherein said rows are rectilinear and wherein said cartridge forming pockets and driver tines of one of said rows are staggered with respect to the cartridge forming pockets and driver tines of the other of said rows.

12. The cartridge and driver assembly of claim 1 wherein said cartridge and said driver are molded of plastic material.

* * * * *